(12) United States Patent
Rindal (10) Patent No.: US 10,881,369 B2
(45) Date of Patent: *Jan. 5, 2021

(54) SYSTEMS AND METHODS FOR ENHANCED RADIOGRAPHY

(71) Applicant: Steven Rindal, Mount Vernon, WA (US)

(72) Inventor: Steven Rindal, Mount Vernon, WA (US)

( * ) Notice: Subject to any disclaimer, the term of this patent is extended or adjusted under 35 U.S.C. 154(b) by 60 days.

This patent is subject to a terminal disclaimer.

(21) Appl. No.: 16/253,073

(22) Filed: Jan. 21, 2019

(65) Prior Publication Data

US 2019/0150868 A1 May 23, 2019

Related U.S. Application Data

(63) Continuation of application No. 14/934,005, filed on Nov. 5, 2015, now Pat. No. 10,182,780.

(60) Provisional application No. 62/075,649, filed on Nov. 5, 2014, provisional application No. 62/238,200, filed on Oct. 7, 2015.

(51) Int. Cl.
*A61B 6/00* (2006.01)
*A61B 6/04* (2006.01)

(52) U.S. Cl.
CPC ............... *A61B 6/505* (2013.01); *A61B 6/04* (2013.01); *A61B 6/4452* (2013.01); *A61B 6/488* (2013.01); *A61B 6/54* (2013.01)

(58) Field of Classification Search
CPC ........ G01N 23/00; G01N 23/02; G01N 23/04; G01N 23/08; G01N 23/083; A61B 6/00; A61B 6/04; A61B 6/0457; A61B 6/44; A61B 6/4452; A61B 6/4458; A61B 6/4476; A61B 6/505; A61B 6/488; A61B 6/54; A61N 5/1048; H05G 1/02
USPC ............ 378/62, 68, 189, 193, 196, 197, 205
See application file for complete search history.

(56) References Cited

U.S. PATENT DOCUMENTS

| | | | |
|---|---|---|---|
| 4,894,855 A | 1/1990 | Kresse | |
| 5,287,546 A | 2/1994 | Tesic et al. | |
| 7,073,939 B2 | 7/2006 | Spahn | |
| 7,231,073 B2 | 6/2007 | Tanaka | |
| 7,341,376 B2 | 3/2008 | Birdwell | |
| 7,391,846 B2 | 6/2008 | Verdonck et al. | |
| 10,182,780 B1 * | 1/2019 | Rindal | A61B 6/505 |

FOREIGN PATENT DOCUMENTS

JP 08289888 A 11/1996

OTHER PUBLICATIONS

U.S. Appl. No. 62/075,649, filed Nov. 5, 2014. First Named Inventor: Rindal.

(Continued)

*Primary Examiner* — Jurie Yun
(74) *Attorney, Agent, or Firm* — Santangelo Law Offices, P.C.

(57) ABSTRACT

A radiography system for a patient comprising an electromagnetic radiation generator, an electromagnetic radiation detector, a generator support, and a detector support. The generator support moves the generator according to a generator sequence specific to the patient. The detector support moves the detector according to a detector sequence specific to the patient.

20 Claims, 6 Drawing Sheets

(56) References Cited

OTHER PUBLICATIONS

U.S. Appl. No. 62/238,200, filed Oct. 7, 2015. First Named Inventor: Rindal.
U.S. Appl. No. 14/934,005, filed Nov. 5, 2015. First Named Inventor: Rindal.

* cited by examiner

SYSTEMS AND METHODS FOR ENHANCED RADIOGRAPHY

PRIORITY CLAIM

This application is a continuation application of U.S. patent application Ser. No. 14/934,005 filed Nov. 5, 2015, which claims priority to, and the benefit of, U.S. Provisional Application Ser. No. 62/075,649, filed on Nov. 5, 2014, and also claims priority to, and the benefit of, U.S. Provisional Application Ser. No. 62/238,200, filed on Oct. 7, 2015. Each aforementioned application and any priority case is hereby incorporated by reference herein in its entirety.

FIELD OF THE INVENTION

The present invention relates to radiography systems and methods and, in particular, to radiography systems and methods configured to generate images of a patient.

BACKGROUND

The term "radiography" will be used herein to refer to the use of electromagnetic radiation to generate an image of the human body. One particular class of radiography devices uses x-rays to create an image that may be used as a diagnostic tool by a wide variety of health care professionals. Radiography systems are typically sold in a variety of configurations and sizes to generate an image or images of an area of the body of particular interest for a given medical condition.

The present invention is of particular relevance to medical conditions related to the human spine, and that application of the present invention will be described herein in detail. However, the principles of present invention may also be used with other areas of a body as will be generally described below.

The human vertebral or spinal column (hereinafter "spine") is formed by a stack of individual bone structures (vertebrae) separated by intervertebral discs (discs). Ligaments extend along the length of the spine. Anomalies in the spine may have adverse health effects.

Radiography images are commonly used to diagnose anomalies of the spine for the purpose of determining appropriate medical treatment. Improvement of the radiography image can lead to improved medical treatment.

The need exists for radiography systems and methods for generating improved radiography images to facilitate the detection and treatment of anomalies of the human spine as well as other areas of a body.

SUMMARY

The present invention may be embodied as a radiography system for a patient comprising a generator, a detector, a generator support, and a detector support. The generator may generate electromagnetic radiation, and the detector may detect electromagnetic radiation. The generator support can permit or cause movement of the generator according to a generator sequence specific to the patient. The detector support can permit or cause movement of the detector according to a detector sequence specific to the patient.

The present invention may also be embodied as a method of generating a radiography image of a patient comprising the following steps. A generator for generating electromagnetic radiation can be provided. An electromagnetic radiation detector can be provided. A generator sequence specific to the patient can be determined. A detector sequence specific to the patient can be determined. The generator may be moved according to the generator sequence. The detector may be moved according to the detector sequence.

The present invention may also be embodied as a system for generating radiographic images such as of a spine of a patient comprising generator, a detector, a generator support, and a detector support. The generator may generate electromagnetic radiation along a propagation plane. The detector may detect electromagnetic radiation. The generator support can permit or cause movement of the generator according to a generator sequence such as specific to the spine of the patient. The detector support can permit or cause movement of the detector according to a detector sequence such as specific to the spine of the patient. The generator sequence can determine a position in space of the propagation plane such as relative to the spine of the patient.

DETAILED DESCRIPTION

Figure 1:
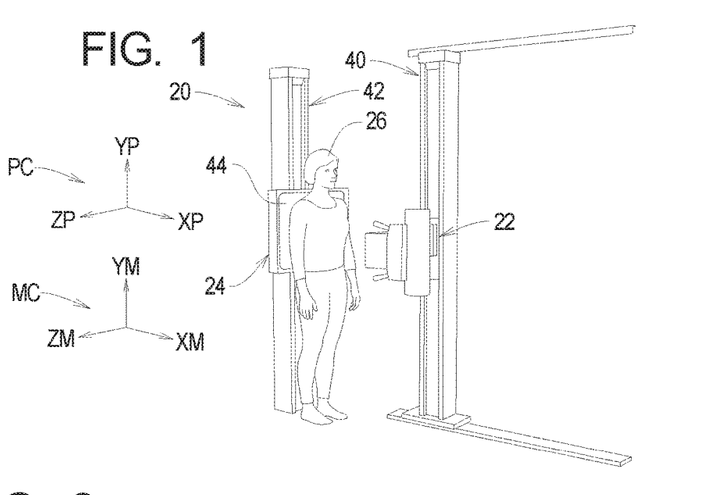
FIG. 1 is a perspective view of a first example x-ray scanning system of the present invention.

Referring initially to FIG. 1 of the drawing, depicted therein is a radiography system 20 constructed in accordance with, and embodying, some principles of the present invention. The radiography system 20 comprises a generator 22 and a detector 24. In use, a patient 26 stands between the generator 22 and the detector 24. The generator 22 projects electromagnetic radiation towards the patient 26. An absorbed portion of the electromagnetic radiation projected towards the patient 26 is absorbed by the patient's body. A passed portion of the electromagnetic radiation projected towards the patient 26 passes through the patient 26 and is received by the detector 24. The detector 24 is either photographic film or a digital detector capable of creating an image representative of the passed portion of electromagnet radiation.

For this example, the human spine typically comprises twenty-four articulating vertebrae and nine fused vertebrae. The vertebrae are arranged in regions typically referred to as the cervical spine (cervical vertebrae C1-C7), the thoracic spine (thoracic vertebrae Th1-Th12), the lumbar spine (lumbar vertebrae L1-L5), the sacrum (S1-S5), and the coccyx (the remaining fused vertebrae).

Figure 2:
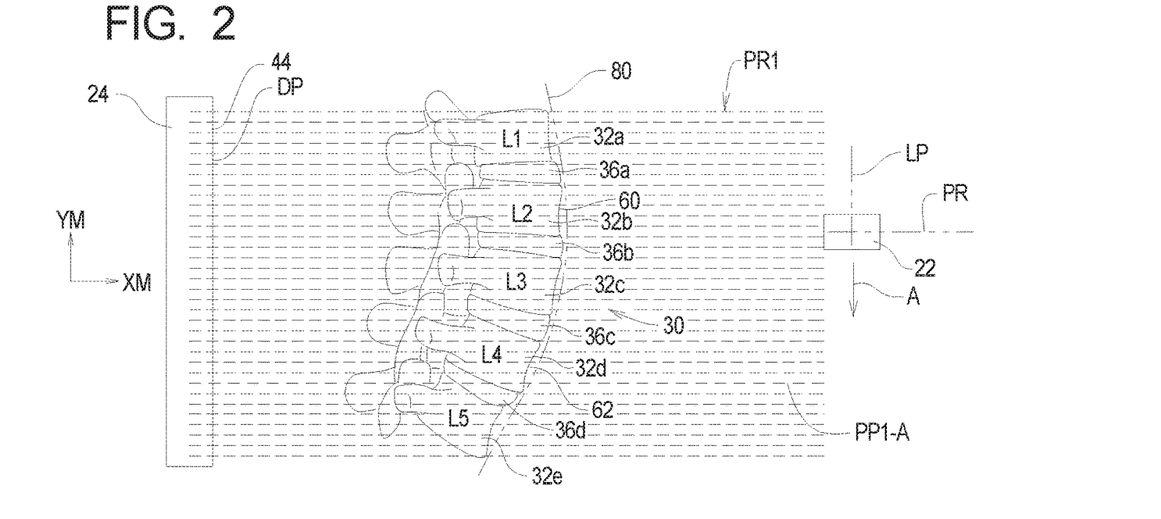
FIG. 2 is a highly schematic side elevation view representing an optional first step in a radiography process, an exposure taken with a patient in a front to back orientation as shown in FIG. 1.
Figure 2A:
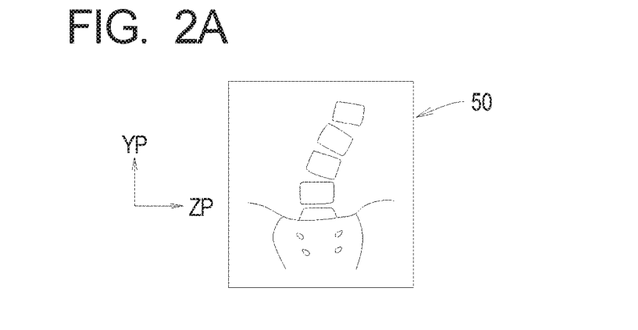
FIG. 2A is a representation of a radiography image generated by the step depicted in FIG. 2.
Figure 3:
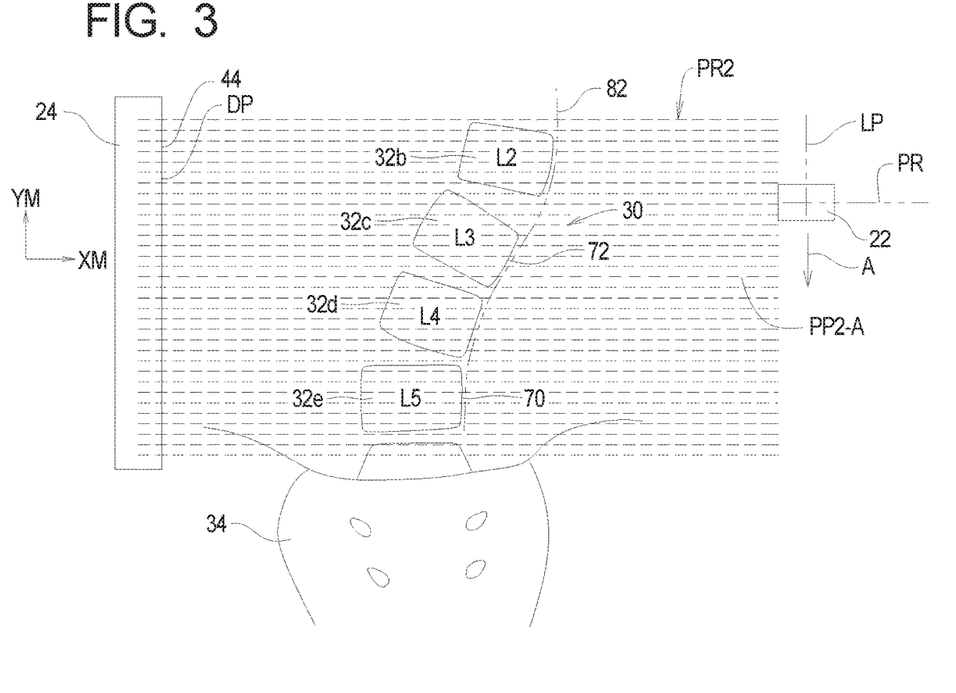
FIG. 3 a highly schematic side elevation view similar to that of FIG. 2 representing an optional step in a radiography process illustrating an exposure taken with a patient in a side orientation.
Figure 7:
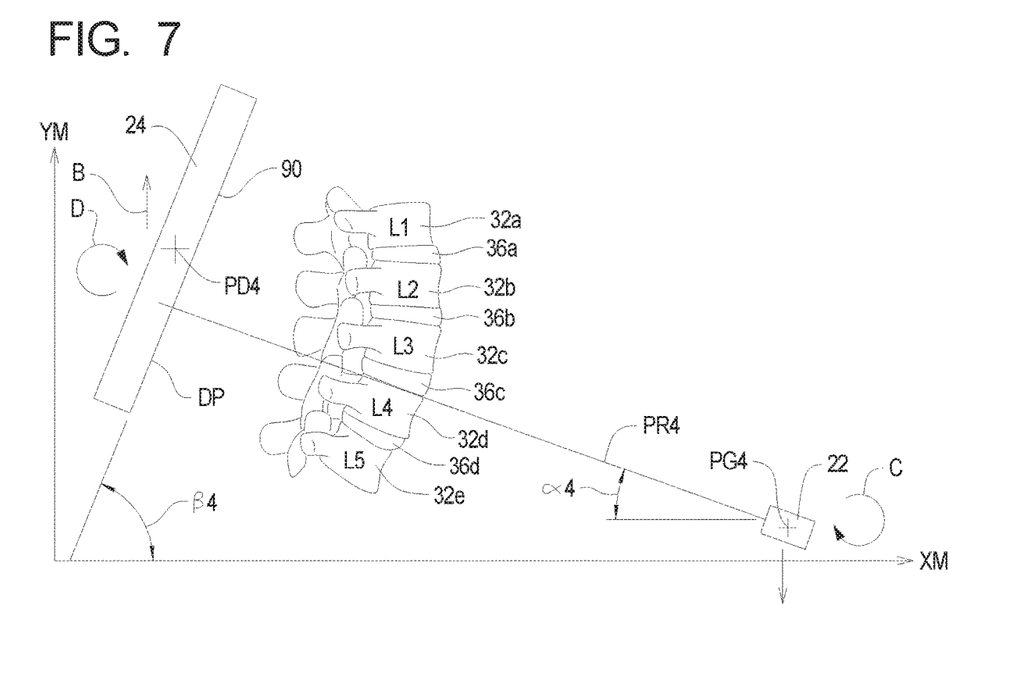
Figure 8:
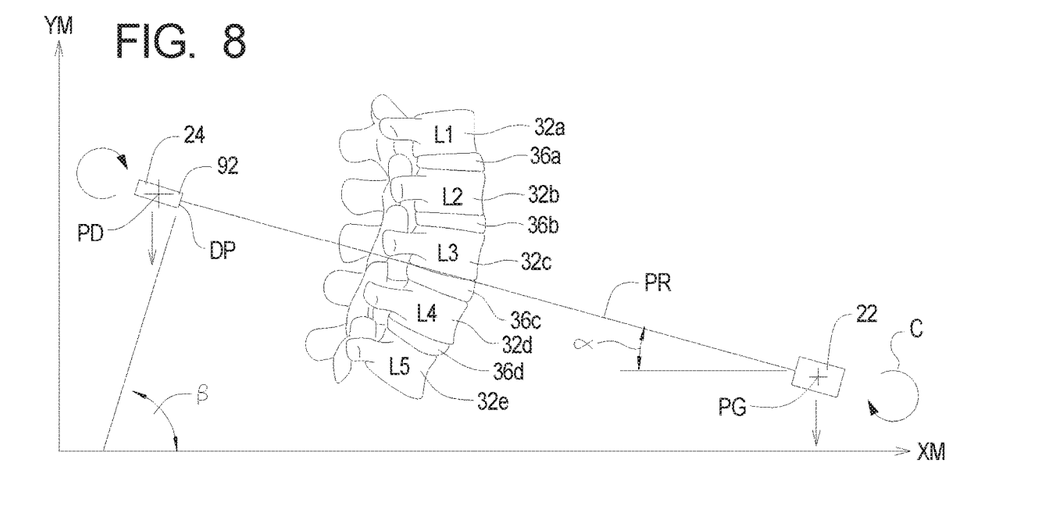
Figure 9:
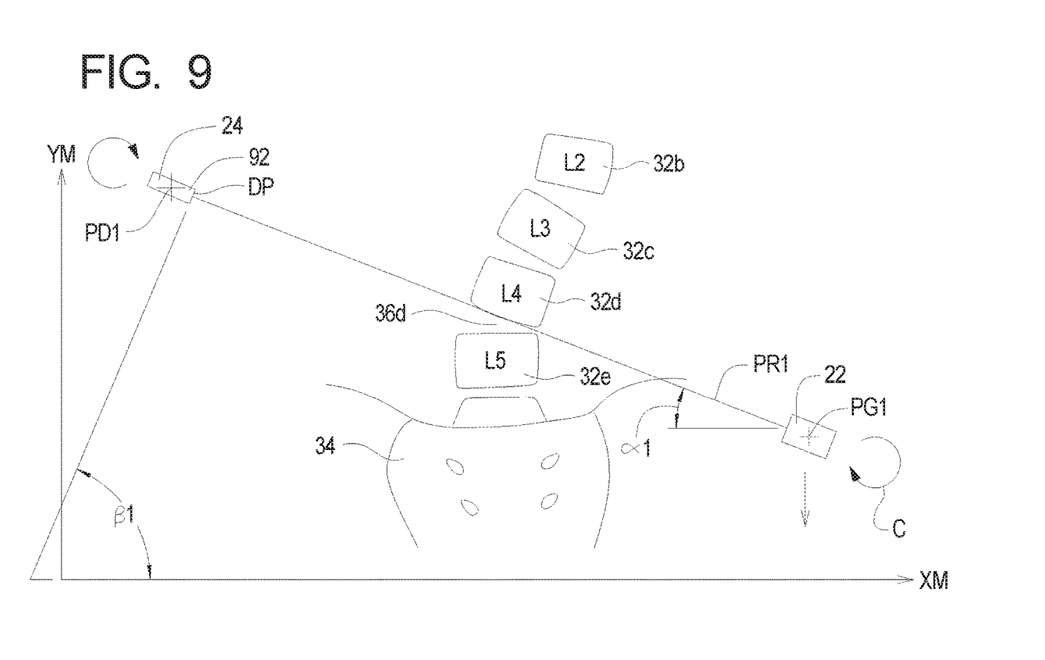
FIGS. 9 and 10 are a highly schematic side elevation views depicting stages of a radiography process of the present invention with a patient in a side orientation.
Figure 10:
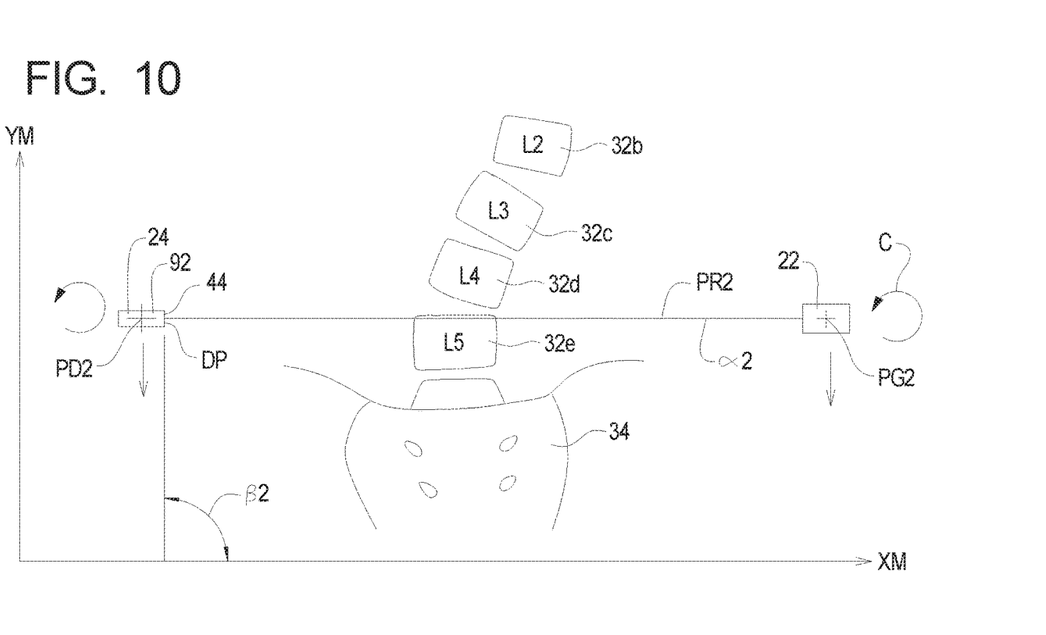

As shown in FIGS. 2-10, the example generator 22 and the example detector 24 are arranged to generate images of a target region 30 comprising a plurality of lumbar vertebrae 32 and a sacrum 34. In particular, FIGS. 2 and 4-8 depict the L1, L2, L3, L4, and L5 lumbar vertebrae 32a, 32b, 32c, 32d, and 32e, while FIGS. 3, 9, and 10 depict the L2, L3, L4, and L5 lumbar vertebrae 32b, 32c, 32d, and 32e. FIGS. 2A, 3, 9, and 10 further depict a portion of the patient's sacrum 34. FIG. 2 illustrates that discs 36 are arranged between adjacent vertebrae 32. For ease of reference, the disc between the L1 and L2 vertebrae 32a and 32b will be referred to as the first disc 36a, the disc between the L2 and L3 vertebrae 32b and 32c will be referred to as the second disc 36b, the disc between the L3 and L4 vertebrae 32c and 32d will be referred to as the third disc 36c, and the disc between the L4 and L5 vertebrae 32d and 32e will be referred to as the fourth disc 36d.

FIG. 1 illustrates that the generator 22 may be supported by a generator support structure 40 and the detector 24 may be supported by a detector support structure 42. FIGS. 2-10 illustrate that the generator 22 can define a projection region PR, and FIGS. 1-10 illustrate that the detector 24 can define a detector surface 44 and a detector plane DP that may be moved during use. Accordingly, FIGS. 2 and 3 schematically depict a series of projection planes at sequential points in time identified by reference characters PP1 (FIG. 2) and PP2 (FIG. 3).

Referring for a moment back to FIG. 1, that figure illustrates a machine coordinate system MC comprising an X-axis XM, a Y-axis YM, and a Z-axis ZM and a patient coordinate system PC comprising an X-axis XP, a Y-axis YP, and a Z-axis ZP. The machine coordinate system MC and patient coordinate system PC are oriented such that the Y-axis can be vertically aligned, while the X- and Z-axes can be horizontally aligned. However, the machine coordinate system MC is oriented with respect to the radiography system 20 such that, for some embodiments, X-axis XM always extends in a direction extending between the generator 22 and the detector 24. In contrast, the X-axis XP of the patient coordinate system PC, can, for some embodiments, be always oriented along front to back (anterior-posterior) directions relative to the patient 26, while the Z-axis ZP, can, for some embodiments, be always oriented along side to side (lateral) directions relative to the patient 26. The Y-axis YP of the patient coordinate system PC can similarly be always oriented along top to bottom (head to toe) directions relative to the patient 26 and is thus vertical when the patient 26 is standing upright.

The orientation of the machine coordinate axis MC and the patient coordinate system PC is arbitrary, but once selected, may be maintained to ensure proper understanding of the radiography images generated by the radiography system 20. Further, it is possible for the machine to be oriented such that the machine Y- and Z-axes YM and ZM are horizontal and the machine X-axis XM is vertical. In this case, the patient will likely be lying on a horizontal support surface with the patient Y- and Z-axes YP and ZP horizontal and the patient X-axis XP vertical.

In FIGS. 2 and 3, the generator support structure 40 supports the generator 22 such that the generator 22 is maintained in a generator plane GP while maintaining the projection region PR in a perpendicular relationship with the generator plane GP. The projection region PR may be the area in which the electromagnetic radiation propagates during the process of generating a radiography image. The projection region PR may be roughly cubic in shape (wide projection region) or may be narrowed down by collimation or generator tube design to be a relatively thin, almost planar shape (narrow or planar projection region). The example projection region PR is configured such that the projection region PR is a wide projection region that projects onto the substantially entire surface of the detector 24 in a conventional manner. The electromagnetic radiation in the projection region PR propagates in a direction perpendicular to both the generator plane GP. When a direction is associated with the propagation region PR, that direction is the direction in which electromagnetic radiation propagates in the projection region.

FIGS. 2 and 3 further illustrate for one embodiment that the detector support structure 42 supports that detector 24 such that the detector plane DP is in a fixed spatial relationship relative to the patient 26. In the example depicted in FIGS. 2 and 3, the detector surface 44 can be adjacent to the target region 30 of the patient 26. Further, FIGS. 2 and 3 illustrate that the detector support structure 42 supports the detector 24 such that the generator plane GP and the detector plane DP are parallel to each other and the projection region PR is perpendicular to both the generator plane GP and the detector plane DP.

And as shown in FIG. 1, the patient 26 is standing upright. In this configuration, the generator plane GP and the detector plane DP are both vertical, and the projection region PR always horizontal. It should be apparent that the patient 26 may be lying prone on the bed and the projection region PR directed up or down through the patient 26 and towards the detector 24 as appropriate.

FIGS. 2 and 3 further illustrate that the generator 22 can be configured to generate a wide projection region and can be fixed such that the projection region PR may be also fixed relative to the fixed detector 24 and the stationary target region 30. Alternatively, with a narrow projection region, the generator 22 may be displaced in the direction of arrow A along the generator plane GP such that the projection region PR is moved relative to the fixed detector 24 and the stationary target region 30. The process of moving the generator 22 relative to the patient 26 while generating a radiography image will be referred to herein as scanning.

Figure 3A:
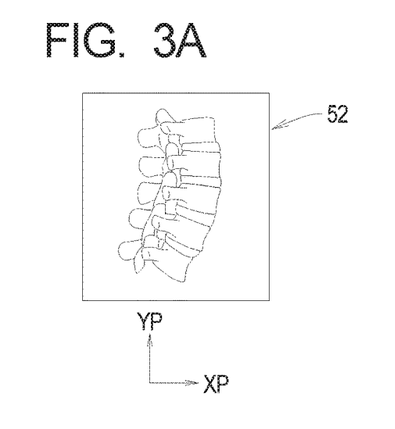
FIG. 3A is a representation of a radiography image generated by the step depicted in FIG. 3.

In FIG. 2, the patient 26 is standing in a side orientation to obtain a lateral view image (i.e., patient Z-axis ZP aligned with machine X-axis XM), and, in FIG. 3 the patient is standing in a front orientation to obtain an anterior view image (i.e., patient X-axis XP aligned with machine X-axis XM). The resulting lateral view image and anterior view image will be referred to as first pilot image 50 (FIG. 2A) and the second pilot image 52 (FIG. 3A). The pilot images 50 and 52 illustrate the orientation of the L2-L5 vertebrae 32b, 32c, 32d, and 32e in lateral and anterior planes, respectively.

As can be seen in FIGS. 2-10, the vertebrae 32 are not perfectly aligned. For example, with reference to FIG. 2 and the patient coordinate system PC, an anterior surface 60 of the L2 vertebrae 32b is substantially parallel to the Y-axis YP and orthogonal to the X-axis XP, while an anterior surface 62 of the L4 vertebrae 32d extends at an angle of approximately thirty degrees with respect to the vertical axis YP and at an angle of approximately sixty degrees with respect to the vertical axis YP. Similarly, with reference to FIG. 3 and the patient coordinate system PC, a first lateral surface 70 of the L5 vertebrae 32e is substantially parallel to the Y-axis YP and orthogonal to the X-axis XP, while a first lateral surface 72 of the L3 vertebrae 32c extends at an angle of approximately thirty degrees with respect to the vertical axis YP and at an angle of approximately sixty degrees with respect to the vertical axis YP. The angles defined by the vertebrae 32 may thus compound such that, not only are the vertebrae angled with respect to either horizontal and vertical, the vertebrae 32 may be arranged along a curved and/or twisted path moving along the spine.

Accordingly, each particular arrangement of vertebrae 32 will thus define at least one curved vertebral path. A first example vertebral path is depicted at 80 in FIG. 2 and is associated with an anterior face of the spine within the target region 30. A second example vertebral path is depicted at 82 in FIG. 3 and is associated with first lateral face of the spine within the target region 30. Additional vertebral paths may be associated with posterior face and second lateral face of the spine within the target region 30.

However, as is apparent from the discussion above and FIGS. 2 and 3, during the process described with reference to FIGS. 2 and 3 the projection region PR may be always parallel to the X-axes XM and XP and to the Z-axes ZM and ZP. Accordingly, with angled vertebrae, images such as the pilot images 50 and 52 generated by the processes described with reference to FIGS. 2 and 3 may not clearly show the details of the space between adjacent vertebrae 32.

For example, FIG. 2 illustrates that, because of the curvature of the spine associated with the example vertebrae 32a-e, a projection plane PP1-A along which electromagnetic radiation in the projection region PR extends through both the L4 vertebrae 32d and the L5 vertebrae 32e. Similarly, FIG. 3 illustrates that the curvature of the spine as defined by the example vertebrae 32b-e requires that a projection region PP2-A extend through both the L3 vertebrae 32c and the L4 vertebrae 32d. The arrangement of the vertebrae 32 in both of these cases may obscure certain details of the vertebrae and/or the disc 36 or vertebral space therebetween.

In the example radiography system 20, a unique image plan comprising a generator sequence and/or a detector sequence can be computed based on the physical structure of a specific patient. The image plan may be embodied as computer code that determines a generator position PG and detector position PD and a propagation angle $\alpha$ and a detector angle $\beta$ at any point in time. In a two dimensional system, the generator position and angle may be generally represented as PG(XM, YM, $\alpha$), while the detector position and angle may be represented as PD(XM, YM, $\beta$). Typically, $\alpha$ and $\beta$ may be complementary. A three dimensional system could use a notation such as PG(XM, YM, ZM, $\alpha1$, $\alpha2$) and PD(XM, YM, ZM, $\alpha1$, $\alpha2$) to represent the generator position and angle and detector position and angle, respectively.

In the example depicted in the drawing, the particular angular relationships among the vertebrae 32 in the target region 30 is shown in the pilot images 50 and 52. In particular, at least some of the relevant angular relationships among individual vertebrae 32 in the target region 30 are shown in the first and second pilot images 50 and 52, and images or data such as that displayed in the pilot images 50 and 52 may be used to generate image plan.

The generator sequence and detector sequences comprising the image plan can determine a positional and directional relationship of the generator 22 and detector 24, respectively, in two or three dimensions to allow the generation of one or more radiography images associated with the shape of a particular spine or other body part. The shape of a particular spine or other body part may be determined based on, for example, data such as one or more of pilot images 50 and 52. In addition, the position and angle of the upper and lower surfaces of the vertebrae 32 may be taken into account when determining one or both of the generator sequence and the detector sequence forming the image plan. The characteristics of a particular spine or the like will determine the image plan, and the image plan may be calculated or developed based on the generator sequence and detector sequence as necessary to allow a meaningful radiographic image to be obtained from the detector 24.

In particular, assuming a known relationship of the patient coordinate system PC with respect to the machine coordinate system MC, the generator 22 and detector 24 may be arranged and oriented within the machine coordinate system MC as necessary to direct the projection region PR so that the projection region PR is substantially orthogonal to a vertebral path associated with the spinal or other face of interest. The relationship of the patient coordinate system PC with respect to the machine coordinate system MC need not be fixed but may be known at any given point in time to compute the generator sequence and/or detector sequence and to understand the resulting radiographic image.

Referring now to FIGS. 4-7, depicted therein is a relatively simple example of the generation of a radiography image or two or more (a plurality) radiography images using the principles of the present invention. For simplicity in describing the example depicted in FIGS. 4-7, the generator 22 and detector 24 are moved from a home position to any one or more points along a generator plane GP (parallel to XM) and angular movement may be limited to a predetermined plane (XM,YM). In a more complex system, the generator 22 and detector 24 may be arranged at any point in three-dimensional space and may be rotated or pivoted to allow angular movement in any direction from that point in three-dimensional space.

In the example depicted in FIGS. 4-7, a generator sequence may be computed that determines a position and angle of the generator 22 at any point in time based on characteristics of the target region 30. The characteristics of the particular target region 30 may be determined based on at least one of the pilot images 50 and 52 described above. Similarly, a detector sequence is computed that may determine a position and angle of the detector 24 at any point in time based on at least one of the pilot images 50 and 52 described above. In the process depicted in FIGS. 4-7, the detector 24 can be formed by a planar structure 90 such as a photographic plate or array of digital sensors. Four example points in time may be depicted in FIGS. 4-7, respectively. These points may be in succession to form a single image (scanning) or may be associated with discrete images taken in any order. In either case, a narrow projection region or a wide projection region may be used.

Figure 4:
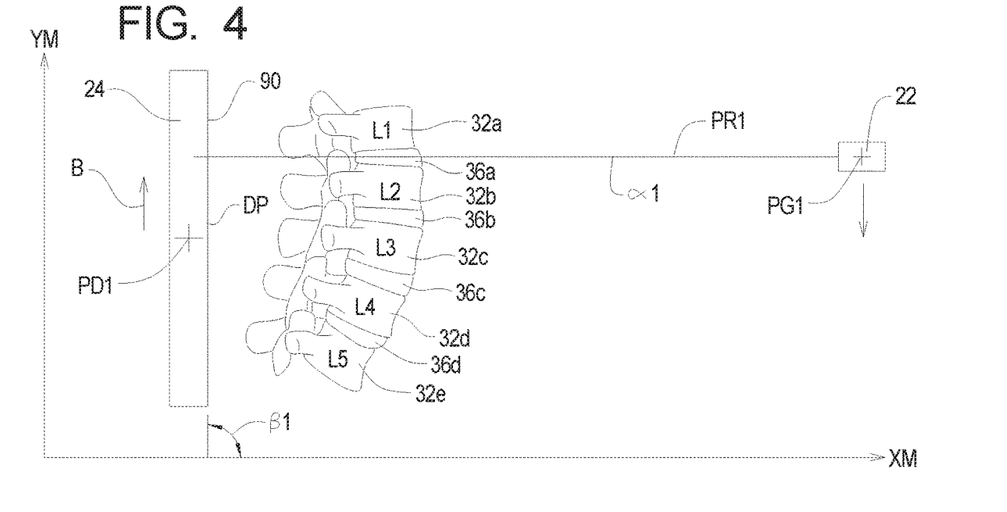
FIGS. 4-8 are a highly schematic side elevation views depicting stages of a radiography process of the present invention with a patient in a front to back orientation.

At a first point in time depicted in FIG. 4, a first projection region PR1 may be directed between the L1 and L2 vertebrae 32a and 32b and through the first disc 36a. In this case, a position and angle of the generator are represented as PG1 and $\alpha1$, respectively, and a position and angle of the detector are represented as PD1 and $\beta1$, respectively. Assuming the first point in time is represented as t1, the system may be characterized using the following notation:

Position $t1=(PG1;\alpha1;PD1;\beta1)$.

In the situation depicted in FIG. 4, the projection region PR1 may be substantially horizontal and the detector plane DP may be substantially vertical, so $\alpha1$ is zero degrees and $\beta1$ is ninety degrees. At least a portion of the image associated with the orientation of the projection region PR1 will thus provide a clear view of the first disc 36a. The detector 24 may be also moved up as shown by arrow B to prevent repeated exposure of the same portion of the film structure 90 during a scanning process.

Figure 5:
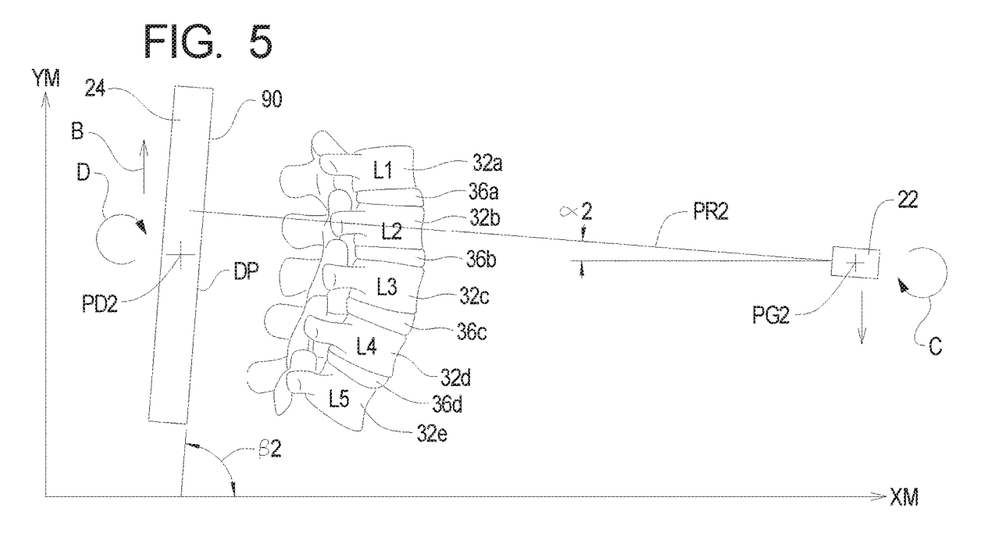

At a second point in time depicted in FIG. 5, a second projection region PR2 may be directed through the L2 vertebrae 32b. In this case, the generator 22 has been rotated as shown by arrow C such that the projection region PR2 is angled slightly with respect to horizontal. The detector 24 has also been rotated as shown by arrow D such that the detector plane DP is angled with respect to vertical to ensure that the second projection region PR2 is substantially orthogonal to the detector plane DP. In this case, a position and angle of the generator are represented as PG2 and α2, respectively, and a position and angle of the detector are represented as PD2 and β2, respectively. Assuming the second point in time is represented as t2, the system may be characterized using the following notation:

Position $t2=(PG2;\alpha2;PD2;\beta2)$.

In the situation depicted in FIG. 5, the projection region PR2 and the detector plane DP may be angled with respect to horizontal, so α2 is approximately twenty degrees and β2 is approximately seventy degrees. At least a portion of the image associated with the projection region PR2 may thus provide a clear view of the L2 vertebrae 32b. Again, the detector 24 may be moved as shown by arrow B to prevent repeated exposure of the same portion of the film structure 90 during a scanning process.

Figure 6:
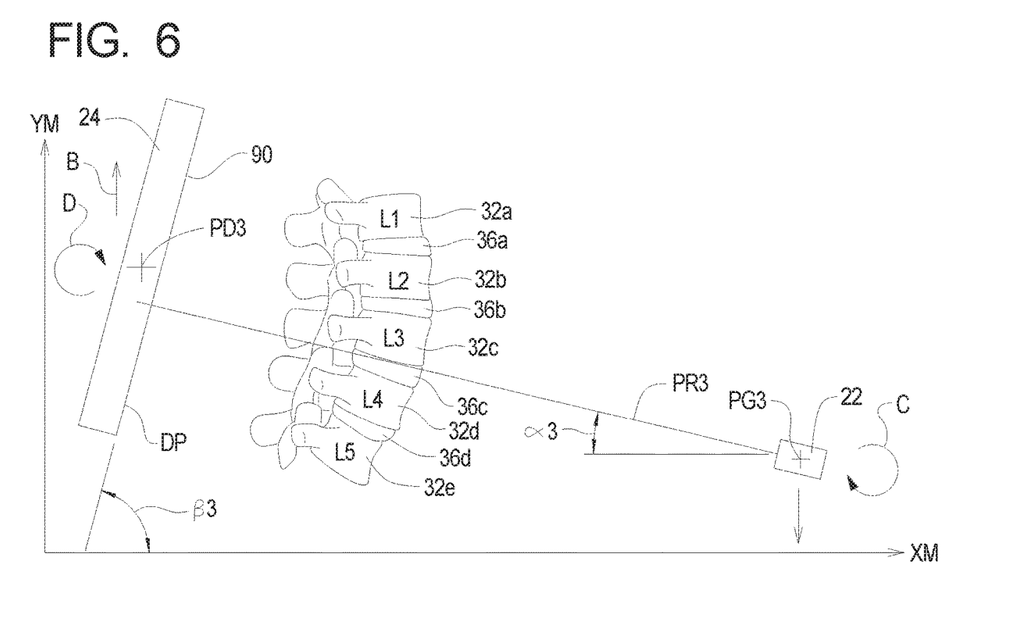

At third and fourth points in time as depicted in FIGS. 6 and 7, third and fourth projection planes PP3 and PP4 may be directed between the L3 and L4 vertebrae 32c and 32d and through the third disc 36c. If the process involves successive exposures taken during a scanning process, the third projection region PR3 at the third point in time indicates the beginning of the scan of the third disc, and the fourth projection region PR4 at the fourth point in time indicates the end of the scan of the third disc.

Again, the generator 22 can be rotated as shown by arrow C such that the projection planes PP3 and PP4 are angled slightly with respect to horizontal. The detector 24 can also rotate as shown by arrow D such that the detector planes DP and DP are angled with respect to vertical to ensure that the projection planes PP3 and PP4 are substantially orthogonal to the detector plane DP. In this case, a position and angle of the generator may be represented as PG3 and PG4 and α3 and α4, respectively, and a position and angle of the detector may be represented as PD3 and PD4 and β3 and β4, respectively. Assuming the third and fourth points in time are represented as t3 and t4, the system may be characterized using the following notation:

Position $t3=(PG3;\alpha3;PD3;\beta3)$.

Position $t4=(PG4;\alpha4;PD4;\beta4)$.

In the situation depicted in FIGS. 6 and 7, the projection planes PP3 and PP4 and the detector plane DP may be angled with respect to horizontal, for example so α3 is approximately thirty degrees, α4 is approximately forty degrees, β3 is approximately sixty degrees, and β4 is approximately 50 degrees. The portion of the image associated with the projection planes PP3 and PP4 will thus provide a clear view of the third vertebral disc 36c. Again, the detector 24 may be moved up as shown by arrow B to prevent repeated exposure of the same portion of the planar film structure 90 during a scanning process.

While four points in time are depicted and described herein, the radiography process may include only a single point in time, more or less than four points in time. Additional points in time may be outside the period bracketed by t1 and t4 and between any of the time points t1, t2, t3, and t4.

The resulting radiography image may be one or more two-dimensional images generally corresponding to the target region 30. If the image is the composite of a plurality of discrete exposures taken as part of a scanning process, the image will correspond to a projection of the spine along a straight line. A scan image may contain less information about characteristics of the spine such as curvature but will provide better information about the individual vertebrae and the vertebral spaces between the vertebrae, including the vertebral discs.

Referring now to FIG. 8, depicted therein is another simple example of the generation of a radiography image using the principles of the present invention. Again, for clarity the generator 22 and detector 24 can be moved along generator plane GP and angular movement can be limited to a predetermined plane. However, the generator 22 and detector 24 may be arranged at any point in three-dimensional space and angular movement may be in any direction from that point in three-dimensional space.

In the example depicted in FIG. 8, a generator sequence can be computed that determines a position and angle of the generator 22 at any sampling time point within a larger sampling time period based on characteristics of the target region 30. The characteristics of the particular target region 30 may be determined based on at least one of the pilot images 50 and 52 described above. Similarly, a detector sequence can be computed that determines a position and angle of the detector 24 at any point in time based on at least one of the pilot images 50 and 52 described above. In the process depicted in FIG. 8, the detector 24 can be formed by a linear digital detector 92 connected to a computer or the like. A single sampling period is depicted in FIG. 8, but, as in FIGS. 4-7, the radiography process implemented by the system of FIG. 8 may be performed over a plurality of points in time.

At the point in time depicted in FIG. 8, a projection region PR can be directed between the L3 and L4 vertebrae 32c and 32d and through the third disc 36c. The projection region PR in FIG. 8 indicates the beginning of the scan of the third disc. Again, during scanning the generator 22 can be rotated as shown by arrow C such that projection region PR can be maintained in a substantially orthogonal orientation to the detector plane DP. In this case, a position and angle of the generator are represented as PG and α, respectively, and a position and angle of the detector are represented as PD and β, respectively. Assuming the point in time is represented as t, the system may be characterized using the following notation:

Position $t=(PG;\alpha;PD;\beta)$.

In the situation depicted in FIG. 8, the projection region PR and the detector plane DP may be angled with respect to horizontal, for example, so α is approximately thirty degrees and β is approximately sixty degrees. The portion of the image associated with the projection region PR is at the beginning of the process of scanning the third vertebral disc 36c.

While only one point in time is depicted and described in FIG. 8, the radiography process will typically include additional points in time before and after the time point t.

With the digital detector 92, the electromagnetic energy impinging on the detector 24 can be sampled, converted into digital data, and used with data from successive positions to generate a radiography image comprised of one or more discrete exposures. The detector sequence controlling movement of the digital detector 92 may need only make sure that the digital detector 92 is located and angled as necessary during the sampling period to obtain a clean sample of the electromagnetic energy associated with a particular data point.

The data collected by the digital detector 92 may be assembled and used to create a two-dimensional image generally corresponding to the target region 30 laid out in a straight line. This image may contain less information about characteristics of spine or other curvature but may provide better information about the individual vertebrae and the vertebral spaces between the vertebrae, including the vertebral discs or the like. In addition, the digital data may be combined with other data associated with the target region 30 to allow at least a portion of a three-dimensional model of the target region 30 to be generated. The three-dimensional model may further be converted into a physical model using computer aided manufacturing.

Referring now to FIGS. 9 and 10, depicted therein is another simple example of the generation of a radiography image using the principles of the present invention. Again, for clarity the generator 22 and detector 24 may be fixed at those one or more discrete locations or may be moved along a linear path with angular movement limited to a predetermined plane, and the generator 22 and detector 24 may be arranged at any point in three-dimensional space and angular movement may be in any direction from that point in three-dimensional space.

In the example depicted in FIGS. 9 and 10, a generator sequence may be computed that determines a position and angle of the generator 22 at any sampling period based on characteristics of the target region 30. The characteristics of the particular target region 30 may be determined based on at least one of the pilot images 50 and 52 described above. Similarly, a detector sequence may be computed that determines a position and angle of the detector 24 at any point in time based on at least one of the pilot images 50 and 52 described above. In the process depicted in FIGS. 9 and 10, the detector 24 can be formed by the digital detector 92 connected to a computer or the like. As in FIGS. 4-7, the radiography process implemented by the system of FIGS. 9 and 10 would in most cases be performed over a plurality of points in time.

In FIGS. 9 and 10, the patient 26 has been rotated relative to the system to obtain a lateral image. In this case, a position and angle of the generator are represented as PG1 and PG2 and $\alpha 1$ and $\alpha 2$, respectively, and a position and angle of the detector are represented as PD1 and PD2 and $\beta 1$ and $\beta 2$, respectively. Assuming the points in time are represented as t1 and t2, the system may be characterized using the following notation:

Position $t1 = (PG1; \alpha 1; PD1; \beta 1)$.

Position $t2 = (PG2; \alpha 2; PD2; \beta 2)$.

In the situation depicted in FIGS. 9 and 10, the projection region PR1 and the detector plane DP2 may be angled with respect to horizontal, for example, so $\alpha 1$ is approximately thirty degrees, $\alpha 2$ is approximately forty degrees, $\beta 1$ is approximately sixty degrees, and $\beta 2$ is approximately 50 degrees. The portion of the image associated with the projection planes PP1 and PP2 will thus provide a clear view of the vertebral space and/or disc between the L4 and L5 vertebrae 32*d* and 32*e*.

While only two points in time are depicted and described herein, the radiography process will typically include additional points in time, both outside the period bracketed by t1 and t2 and between the time points t1 and t2.

At the points in time depicted in FIGS. 9 and 10, a projection region PR1 and PR2 may be directed between the L4 and L5 vertebrae 32*d* and 32*e*. These two projection regions PR1 and PR2 may be associated with discrete exposures forming separate radiography images or may be associated with the beginning and the end of a scanning process involving more than two exposures. In the case of a scan, the projection region PR1 in FIG. 9 indicates the beginning of the scan, while the projection region PR2 in FIG. 10 indicates the end of the scan. Again, the generator 22 may be rotated as shown by arrow C such that projection region PR may be maintained in a substantially orthogonal orientation to the detector plane DP during scanning.

With the digital detector 92, the electromagnetic energy impinging on the detector 24 can be sampled, converted into digital data, and stored for future processing. The detector sequence controlling movement of the digital detector 92 can ensure that the detector 92 is located and angled as necessary during the sampling period to obtain a clean sample of the electromagnetic energy associated with a particular data point.

The data collected by the digital detector 92 may be assembled and used to create one or more two-dimensional images. With an image created by a scanning process involving a succession of exposures, the image will generally correspond to the target region 30 laid out in a straight line. This image will contain less information about certain spinal characteristics such as spinal curvature but will provide better information about the individual vertebrae and the vertebral spaces between the vertebrae, including the vertebral discs as but one example. In addition, the digital data may be combined with other data associated with the target region 30 to allow at least a portion of a three-dimensional model of the target region 30 to be generated. The three-dimensional model may further be converted into a physical model using computer aided manufacturing.

A number of robotic systems may be used as or as part of the generator support structure 40 and detector support structure 42 to position and angle the generator 22 and the detector 24. As one example, the generator 22 and detector 24 may be supported for linear movement and rotation in a single plane as shown in FIGS. 4-10. Alternatively, a multiple axis robotic arm may be used to move the generator 22 and/or detector 24 in three-dimensional space and also to rotate through the XM-YM plane and the XM-ZM plane.

The generator and detector sequences forming the image plan may direct a sequence of movements required to displace the generator 22 and detector 24 from a home position to a position at which a desired projection region may be obtained, at which point an exposure can be taken. And if multiple images are desired or a scanning process employing multiple exposures is performed to obtain a single image, the generator and detector sequences can include the machine control commands and/or feedback necessary to move the generator 22 and detector 24 to a plurality of positions. In this case, one or more exposures may be taken at each of the plurality of positions.

Figure 11:
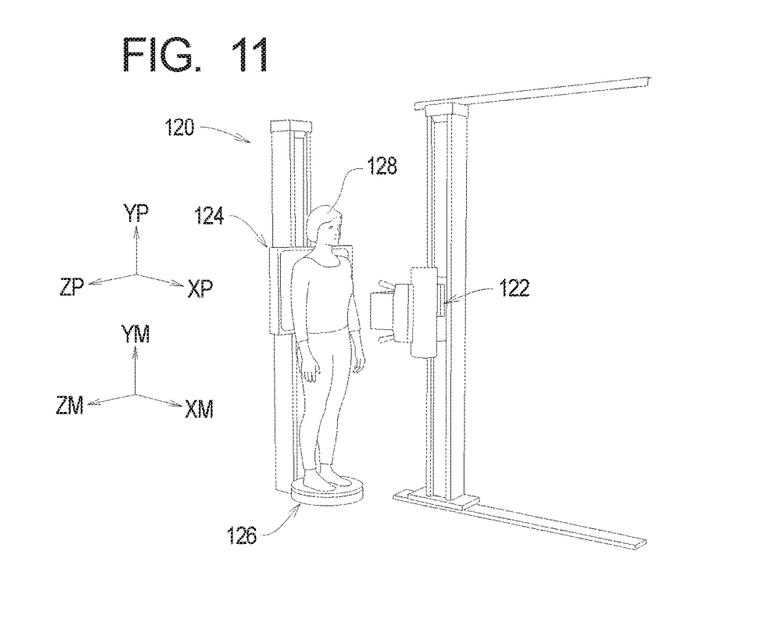
FIG. 11 is a perspective view of a second example x-ray scanning system of the present invention.

Turning now to FIG. 11, depicted therein is a second example radiography system 120 of the present invention. The radiography system 120 comprises a generator 122, a detector 124, and a platform 126. In use, a patient 128 stands on the platform 126 between the generator 122 and the detector 124. The generator 122 projects electromagnetic radiation towards the patient 26. When a platform 126 is provided, the image plan may further comprise a platform sequence for controlling movement of the platform 126. The platform sequence may also be calculated based on data such as the pilot images 50 and 52 described above. The platform 126 can define an axis of rotation parallel to the machine y-axis YM and can be controllable to move the patient such that the patient 26 rotates about the patient y-axis YP.

As the generator 122 and detector 124 move according to generator and detector sequences as generally described above, the platform 126 rotates according to a patient platform sequence. As the absorbed portion of the electromagnetic radiation projected towards the patient 128 is absorbed by the patient's body, the patient's body may be rotated such that twist or other curvature of the spine is taken into account as the scan is performed. The passed portion of the electromagnetic radiation that is passed through the patient 128 and is received by the detector 124 may thus contain information that is not obscured by asymmetrical twists or other curvature aside from front to back or side to side.

In the second example radiography system 120, the use of the platform sequence to control rotation of the platform 126 in the XM-ZM plane can allow the use of generator and detector support systems that allow linear movement and rotation in a single plane as shown in FIGS. 4-10 yet obtain data/images similar to that obtained by a three-dimensional, multiple plane system.

What is claimed is:

1. A radiography system for a patient comprising:
an electromagnetic radiation generator that generates electromagnetic radiation, wherein the electromagnetic radiation is transmitted along a substantially planar projection region;
an electromagnetic radiation detector, where the detector defines a detector plane;
a generator support that supports the generator to permit continuous movement of the generator according to a sequence specific to the patient; and
a detector support that supports the detector to permit continuous movement of the detector according to a sequence specific to the patient; whereby
as the generator support continuously moves the generator, the generator continuously generates electromagnetic radiation along the projection region; and
the detector support further continuously moves the detector such that the detector is displaced relative to the generator and the detector plane is continuously supported in a desired angular relationship relative to the projection region such that the electromagnetic radiation generated by the generator is continuously received by the detector, and a radiographic image is formed from the detector.

2. A radiography system as recited in claim 1, in which the sequence of movement of the generator determines a position in space of the projection region relative to the patient.

3. A radiography system as recited in claim 1, in which the sequence of movement of the generator determines a spatial position of and propagation angle associated with the generator.

4. A radiography system as recited in claim 1, in which:
the generator support permits linear movement and rotation within a predetermined plane; and
the detector support permits linear movement and rotation within the predetermined plane.

5. A radiography system as recited in claim 4, further comprising a patient platform that permits rotation relative to at least one of the generator and the detector.

6. A radiography system as recited in claim 1, in which:
the generator support permits movement within three-dimensional space and rotation within first and second predetermined planes; and
the detector support permits movement within three-dimensional space and rotation within first and second predetermined planes.

7. A radiography system as recited in claim 1, in which the sequence of movement of the generator and the sequence of movement of the detector are determined based on characteristics of the patient.

8. A radiography system as recited in claim 1, in which the sequence of movement of the generator and the sequence of movement of the detector are determined based on at least one pilot image of the patient.

9. A method of generating a radiography image of a patient comprising the steps of:
providing an electromagnetic radiation generator that transmits electromagnetic radiation along a substantially planar projection region;
providing an electromagnetic radiation detector, where the detector defines a detector plane;
determining a generator sequence specific to the patient;
determining a detector sequence specific to the patient;
causing continuous movement of the generator according to the generator sequence; and
causing continuous movement of the detector according to the detector sequence; and
as the generator is continuously moved according to the generator sequence, operating the generator to continuously generate electromagnetic radiation along the projection region, and
continuously displacing the detector in accordance with the detector sequence such that the detector is displaced relative to the generator and the detector plane is continuously supported in a desired angular relationship relative to the projection region such that
the electromagnetic radiation generated by the generator is continuously received by the detector, and
a radiographic image is formed from the detector.

10. A method as recited in claim 9, in which the step of determining the generator sequence comprises the step of determining a position in space of the projection region relative to the patient.

11. A method as recited in claim 9, in which the step of determining the generator sequence comprises the step of determining a spatial position of and propagation angle associated with the generator.

12. A method as recited in claim 9, in which:
the generator is linearly moved and rotated within a predetermined plane; and
the detector is linearly moved and rotated within the predetermined plane.

13. A method as recited in claim 12, further comprising the step of rotating the patient relative to at least one of the generator and the detector.

14. A method as recited in claim 9, in which:
the generator is moved within three-dimensional space and rotated within first and second predetermined planes; and
the detector is moved within three-dimensional space and rotated within first and second predetermined planes.

15. A method as recited in claim 9, in which the generator sequence and the detector sequence are determined based on characteristics of a spine of the patient.

16. A method as recited in claim 9, further comprising the step of generating at least one pilot image of a spine of the patient, where the generator sequence and the detector sequence are determined based on the at least one pilot image.

17. A system for generating a radiographic image of a patient comprising:
   an electromagnetic radiation generator that transmits electromagnetic radiation along a substantially planar projection region;
   an electromagnetic radiation detector, where the detector defines a detector plane;
   a generator support that supports the generator to permit continuous movement of the generator according to a sequence specific to the patient; and
   a detector support that supports the detector to permit continuous movement of the detector according to a detector sequence specific to the patient; wherein
   the sequence of movement of the generator determines a position in space of the projection region relative to the patient; and
   as the generator support permits continuous movement of the generator, the generator continuously generates electromagnetic radiation along the projection region; and
   the detector support further permits continuous movement of the detector such that the detector is displaced relative to the generator and such that the detector plane is continuously supported in a desired angular relationship relative to the projection region, such that the electromagnetic radiation generated by the generator is continuously received by the detector, and
   a radiographic image is formed from the detector.

18. A system for generating a radiographic image as recited in claim 17, in which:
   the generator support permits linear movement and rotation within a predetermined plane; and
   the detector support permits linear movement and rotation within the predetermined plane.

19. A system for generating a radiographic image as recited in claim 18, further comprising a platform for supporting the patient for rotation relative to at least one of the generator and the detector.

20. A system for generating a radiographic image as recited in claim 17, in which:
   the generator support permits movement within three-dimensional space and rotation within first and second predetermined planes; and
   the detector support permits movement within three-dimensional space and rotation within first and second predetermined planes.

* * * * *